(12) United States Patent
Sinha

(10) Patent No.: US 7,230,095 B2
(45) Date of Patent: Jun. 12, 2007

(54) IMMOBILIZATION OF OLIGONUCLEOTIDES ONTO SOLID SUPPORTS

(75) Inventor: Nanda Dulal Sinha, Milford, MA (US)

(73) Assignee: Avecia Biotechnology Inc., Milford, MA (US)

( * ) Notice: Subject to any disclaimer, the term of this patent is extended or adjusted under 35 U.S.C. 154(b) by 234 days.

(21) Appl. No.: 10/475,298

(22) PCT Filed: Apr. 25, 2002

(86) PCT No.: PCT/GB02/01912

§ 371 (c)(1),
(2), (4) Date: Oct. 21, 2003

(87) PCT Pub. No.: WO02/088160

PCT Pub. Date: Nov. 7, 2002

(65) Prior Publication Data

US 2005/0048487 A1 Mar. 3, 2005

(51) Int. Cl.
*C07H 21/00* (2006.01)
*C07H 21/02* (2006.01)
*C12Q 1/68* (2006.01)

(52) U.S. Cl. .................. 536/25.3; 435/6; 536/25.33

(58) Field of Classification Search .................. 435/6; 536/25.3, 25.33
See application file for complete search history.

(56) References Cited

U.S. PATENT DOCUMENTS

| | | | |
|---|---|---|---|
| 5,436,327 A * | 7/1995 | Southern et al. ......... | 536/25.34 |
| 5,589,586 A * | 12/1996 | Holmberg .................. | 536/25.3 |
| 5,869,696 A * | 2/1999 | Reddy et al. ............... | 548/564 |
| 6,013,789 A * | 1/2000 | Rampal ..................... | 536/25.3 |
| 2004/0106728 A1* | 6/2004 | McGall et al. ............. | 525/54.1 |

FOREIGN PATENT DOCUMENTS

| | | |
|---|---|---|
| EP | 0117777 A1 | 9/1984 |
| EP | 0511559 A1 | 4/1992 |
| WO | WO 90/09393 | 8/1990 |
| WO | WO 92/08728 | 5/1992 |
| WO | WO 94/19364 | 9/1994 |
| WO | WO 01/92566 | 12/2001 |

* cited by examiner

*Primary Examiner*—Jezia Riley
(74) *Attorney, Agent, or Firm*—Morgan Lewis & Bockius LLP

(57) ABSTRACT

A solid support bound polynucleotide, preferably a 3'-O- or 5'-O-substituted polynucleotide, is disclosed. The polynucleotides are of formula:

$$Q-O-\underset{\underset{OH}{|}}{\overset{\overset{X}{\|}}{P}}-O-Y-O-\underset{\underset{OH}{|}}{\overset{\overset{X}{\|}}{P}}-R$$

wherein Q is a substantially pure polynucleotide, each X is O or S; Y is an inert spacer group; R represents the solid support. Also disclosed is a method of isolating a target biomolecule, preferably a protein or a polynucleotide, from a mixture.

18 Claims, No Drawings

IMMOBILIZATION OF OLIGONUCLEOTIDES ONTO SOLID SUPPORTS

BACKGROUND OF THE INVENTION

Biomolecules immobilized onto solid supports have great utility as affinity reagents, which are often utilized to bind and separate target molecules from mixtures. Oligonucleotides are one example of biomolecules which can be used for this purpose. For example, oligonucleotides can hybridize with complementary sequences. In addition, oligonucleotides having sequences found at regulatory regions can bind with regulatory proteins having specificity for those regions. Thus, affinity reagents comprising solid supports with immobilized oligonucleotides could be used inter alia in the purification, identification and isolation of complementary oligonucleotides and regulatory proteins.

Current methodologies for attaching oligonucleotides to solid phase supports have a number of shortcomings. For example, some methods result in non-specific attachment of the oligonucleotide or can cause side reactions. Methods which are specific typically involve attaching reactive groups directly to the 5' or 3' terminus of the oligonucleotide. Direct attachment at either terminus brings the oligonucleotide into close proximity with the solid support, which can prevent the oligonucleotide from adapting the proper configuration for binding with the target molecule. Other methods require significant manipulation of the matrix and oligonucleotide and are inconvenient to use.

Thus, there is a need for new methods of attaching oligonucleotides to the solid matrices which are convenient to use, site specific, result in minimal or no side reactions and which allow the oligonucleotide to adapt the proper orientation for binding with target molecules.

SUMMARY OF THE INVENTION

It has now been found that alkyl phosphate linking groups attached to polynucleotides, especially the 3' end of polynucleotides, can be used to covalently bind the polynucleotide to solid supports. For example, the derivatized oligonucleotides GGTTGGTGTGGTTGG-OPO-(O-hexyl)-phosphate (SEQ ID NO: 1) (Thrombin binding aptamer) and TAATATGACTCACTATAGGTAACT T-OPO-(O-hexyl)-phosphate (SEQ ID NO: 2) were prepared and attached by the terminal phosphate to amino sepharose by means of a carbodiimide mediated coupling (Example 2). Based on this discovery, novel substrates with bound oligonucleotides, methods of purifying and/or isolating biomolecules with said substrates and methods of preparing said substrates are disclosed herein.

According to the present invention, there is provided a solid support bound polynucleotide of the formula (A):

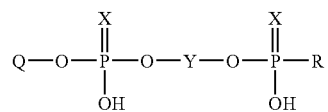

wherein:
Q is a substantially pure polynucleotide;
each X is independently O or S;
Y is an inert spacer group; and
R is a solid support.

One embodiment of the present invention is a solid support bound 3'-O-substituted polynucleotide. The 3'-O-substituent is represented by Structural Formula (I):

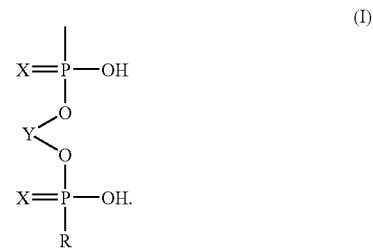

Each X is independently S or O; Y is an inert spacer group; R is a solid support; and the 3'-O-substituted polynucleotide is substantially pure. Preferably each X is O.

Another embodiment of the present invention is a method of isolating a target biomolecule from a mixture. The method comprises the steps of providing a solid support bound 3'-O-substituted polynucleotide, wherein the 3'-O-substituted polynucleotide can selectively bind the target biomolecule and the 3'-O-substituent is represented by Structural Formula (I) above. The mixture is contacted with the solid support bound 3'-O-substituted polynucleotide under conditions suitable for binding the target biomolecule to the 3'-O-substituted polynucleotide.

Another embodiment of the present invention is a method of preparing a solid support bound polynucleotide. The method comprises the step of esterifying or amidating the terminal phosphate of a 3'-O-substituted polynucleotide with an amine or hydroxyl group that is pendent from a solid support. The 3'-O-substituent is represented by Structural Formula (II):

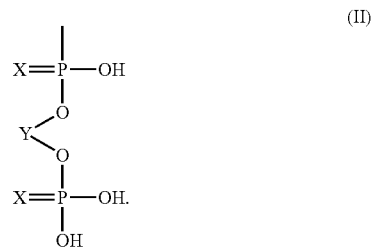

Y and X are as described for Structural Formula (I).

The 3'-O-substituted polynucleotides described herein can be readily and conveniently bonded covalently to solid supports in a site specific manner with minimal side reactions. Thus, the solid support bound 3'-O-substituted polynucleotides can be prepared in high purity and yield. In addition, the spacer group is advantageously of sufficient length so that target molecules can bind to the 3'-O-substituted polynucleotide with minimal or no interference from the solid support. Thus, the solid support bound 3'-O-substituted polynucleotides provide a convenient tool for isolating target biomolecules from mixtures.

DETAILED DESCRIPTION OF THE INVENTION

The present invention is directed to a substantially pure polynucleotide that is bonded to or immobilized onto a solid support by means of a linker group that replaces the 3' terminal hydroxy group on the polynucleotide. The linker is represented by Structural Formula (III):

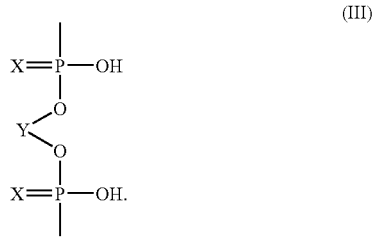

(III)

X and Y are as described for Structural Formula (I).

It is to be understood that the present invention is described with respect to 3'-O-substituted polynucleotides. However, the invention also includes the corresponding solid support bound 5'-O-substituted polynucleotide, i.e, a substantially pure polynucleotide that is bonded to or immobilized onto a solid support by means of a linker group that replaces the 5' terminal hydroxy group on the polynucleotide. The linker is represented by Structural Formula (III). The solid support bound 5'-O-polynucleotide has the analogous utilities and can be prepared by suitable adaptations of the methods used to prepared the corresponding 3'-O-substituted composition. Additionally, it is to be understood that the invention includes support-bound 2'-O-substituted polynucleotides. The linker is represented by Structural Formula (III). The solid support bound 2'-O-polynucleotide has the analogous utilities and can be prepared by suitable adaptations of the methods used to prepared the corresponding 3'-O-substituted composition. Further, the invention also includes polynucleotides bonded to or immobilized onto a solid support via a point of attachment on a nucleobase. Such attachment can be achieved by derivatising the nucleobase with a suitable means of attachment to the linker of Structural Formula (III), for example by the formation of an aminoalkanol, such as an aminohexanol, moiety.

In many embodiments, the supported polynucleotide is not a spiegelmer, particularly not a espielgelmer having the sequence

```
GCGGCGGAGGGTGGGCTGGGGCTGGGCCGGGGGC (SEQ ID No: 3)
GTGCGTAAGCACGTAGCCTCGCCGC.
```

Y in Structural Formulae (A) and (I)–(III) is an inert spacer group. As used herein, an "inert spacer group" is a moiety which, when bonded to the 3' end of a polynucleotide, does not interfere with solid phase synthesis of the polynucleotide and which does not significantly reduce the affinity or selectivity of the polynucleotide with respect to target molecules which bind to the polynucleotide. In many cases, the disclosed solid support bound 3'-O-substituted polynucleotides bind with greater affinity to target molecules than the corresponding unsubstituted polynucleotide when bound directly to the solid support at the 3' terminus. Examples of suitable inert spacer groups include polyalkyleneglycol groups (i.e., Y is —$(CH_2)_n$—[$O(CH_2)_n$]$_m$—, wherein n is 2 or 3 and m is an integer from 0 to about 4), straight chain hydrocarbyl groups and straight chained hydrocarbyl groups in which two or three of the carbon atoms in the chain are replaced with a 1,4-phenylene group. Preferably, the polyalkylene glycol and straight chain hydrocarbyl group are up to about fifteen atoms in length, more preferably from two to ten atoms in length. Hydrocarbyl and polyalkylene glycol spacer groups can be substituted with groups which do significantly interfere with the synthesis of the polynucleotide or its affinity for target molecules, as described above. Examples of suitable substituents include —F, —Cl, —Br, —I, —$CH_3$ or ethyl. However, hydrocarbyl and polyalkylene glycol spacer groups are preferably unsubstitituted. More preferably, the inert spacer group is a C3–C10 straight chained, unsubstituted alkylene group and even more preferably C5–C7 straight chained alkyl group.

The solid support bound 3'-O-substituted polynucleotides of the present invention are prepared by standard methodology for solid phase polynucleotide synthesis. For example, 1-O-(dimethoxytrityl)-ω-[N,N-diisopropylamino-β-cyanoethoxy-phosphino]-1,ω-alkanediol is coupled to a solid phase support suitable for solid phase polynucleotide synthesis using standard phosphoramidite chemistry. One example of a solid support suitable for solid phase polynucleotide synthesis is succinylated silyl amine. A succinylated silyl amine is prepared by derivatizing silica to contain a silyl amine, for example, by reacting silica with 3'-aminopropyl triethoxysilane, and then succinylating the free amine. Other examples of suitable solid supports include succinylated control pore glass (hereinafter "CPG"), and CPG-CO—$CH_2CH_2$—CO—O—$CH_2CH_2$—$SO_2$—$CH_2CH_2OH$. The preparation of 1-O-(dimethoxytrityl)-ω-[N,N-diisopropylamino-β-cyanoethoxy-phosphino]-1,ω-alkanediols and their coupling to solid phase supports is described in Seela and Kaiser, *Nucleic Acids Research* 15:3113 (1987), Wilk, et al., *Nucleic Acids Res.* 18:2065 (1990) and Nelson et al., *Nucleosides Nucleotides* 16:1951 (1997). The entire teachings of these references are incorporated herein by reference.

Following attachment of 1-O-(dimethoxytrityl)-ω-[N,N-diisopropylamino-β-cyanoethoxy-phosphino]-1,ω-alkanediol to the solid support, synthesis of the polynucleotides carried out under standard protocol. The protocol is typically the following four step cycle: 1) removal of the trityl protecting group with, for example dichloroacetic acid in methylene chloride (2:100 v/v) or 20% acetic acid; 2) condensation with a nucleoside phosphoramidite, e.g., 5'-O-DMT-2'-deoxynucleoside 3'-O-(2-cyanoethyl-N,N'-diisopropyl) phosphoramidite, to form a phosphite triester; 3) acylation or capping of unreacted 5'-hydroxyl groups with, for example, acetic anhydride and dimethylaminopyridine/tetrahydrofuran/lutidine (6:90:10 v/v/v); and 4) oxidation of the phosphite triester to phosphate triester with, for example, iodine solution. Once the synthesis is completed, the polynucleotide is freed of protecting groups and cleaved from the solid support, typically with concentrated ammonium hydroxide.

The solid support bound 3'-O-substituted polynucleotides of the present invention include 3'-O-substituted polydeoxynucleotides, 3'-O-substituted polyribonucleotides and mixed 3'-O-polydeoxy and polyribonucleotides. When preparing 3'-O-substituted polyribonucleotides, the 2'-hydroxyl group must be protected during solid phase synthesis and the subsequent attachment of the 3'-O-polyribonucleotide to the solid support.

Also included are solid support bound 3'-O-substituted polynucleotides with modifications in one or more of the purine or pyrimidine groups, e.g., 5-halogenated thymidine, cytosine or uracil; thymidine, cytosine or uracil modified in the 5 position with propyne; or adenosine or guanine in which the 7-nitrogen is replaced with —CH—. Also included are solid support bound 3'-O-substituted polynucleotides substituted at the 2' position of one or more deoxyribose groups with, e.g., —O-(protecting group), —O—CH$_3$, —F—CH$_2$OCH$_3$, —OCH$_2$CH$_2$OCH$_3$ and the like.

During each cycle of solid phase polynucleotide synthesis, a small percentage (typically from 1%–2%) of the polynucleotides fail to couple with the 5'-O-DMT-2'-deoxynucleoside phosphoramidite. Thus, the level of impurities increases with each cycle of the synthesis. The unreacted oligomers are preferably "capped" during each cycle of the synthesis to prevent further extension of these unreacted oligomers during subsequent synthesis cycles, thereby facilitating removal of these impurities from the final product. The product polynucleotide can be separated from the "failed" capped polynucleotides by any suitable method. Typically, separation can be achieved by gel electrophoresis, ion exchange chromatography or reversed phase high pressure liquid chromatography (HPLC).

"Substantially pure polynucleotide" refers to a polynucleotide which has been prepared by synthesis and then purified to be substantially free of "failed" capped polynucleotides, e.g., at least about 90.0% free by weight, preferably at least about 95.0% free by weight and more preferably at least about 98.0% free by weight. Typically, the 3'-O-substituted polynucleotides described herein are purified to remove the capped intermediates before they are covalently bonded to solid support for use in separating biomolecules from mixtures.

Generally, the present invention includes solid support bound 3'-O-substituted polynucleotides without limitation with respect to length. Preferably, however, the polynucleotides are less than about 100 nucleobases in length, more preferably less than about 75 and even more preferably less than about 50 in length. Typically, the solid support bound 3'-O-substituted polynucleotides are at least about 8 nucleobases in length and preferably between about 10 and 35 in length.

Suitable solid supports for the solid support bound 3'-O-substituted polynucleotide are those which can form stable covalent bonds with primary phosphate groups. Such solid supports typically have amine, hydroxyl groups or thiol groups pendent from a polymer backbone or bonded to a linker that is pendent from a polymer backbone. Examples of suitable solid support include without limitation amino sepharose, amino polystyrene, amino silica beads (silica derivatized with amino), silica controlled pore glass beads and an acrylate or methacrylate base amino support.

3'-O-Substituted polynucleotides can be coupled to a solid support containing pendent primary amine groups by any suitable method for preparing phosphoramides from primary amines and phosphates. 3'-O-Substituted polynucleotides can be coupled to a solid support containing pendent hydroxyl groups by any suitable method for preparing phosphate esters from alcohols and phosphates. Typically, an activated phosphate ester is formed in situ with a "coupling agent". The coupling agent reacts with a hydroxyl group of the phosphate, converting the hydroxyl into a leaving group which is susceptible to nucleophilic displacement by, for example, a primary amine or alcohol. Examples of coupling agents include 1,1'-carbonyldiimidazole (CDI), isobutyl chloroformate and carbodiimide coupling agents such 1-(3-dimethylaminopropyl)-3-ethyl-carbodiimide (EDC) and dicyclohexyl carbodiimide (DCC). EDC is a preferred coupling agent.

The solid support bound 3'-O-substituted polynucleotides of the present invention can be utilized to separate biomolecules from mixtures. A 3'-O-substituted polynucleotide is selected which selectively binds to the target biomolecule. "Selectively binds" is defined to mean that the 3'-O-substituted polynucleotide has greater affinity for the target than other components of the mixture, preferably at least twice the affinity, more preferably at least five times the affinity and even more preferably at least ten times the affinity. For example, if the target molecule is an RNA or DNA, a 3'-O-substituted polynucleotide is selected which is sufficiently complementary to the target such that the 3'-O-substituted polynucleotide can hybridize to the target and form a polynucleotide duplex. 3'-O-Substituted polynucleotides can also separate proteins from mixtures, provided that the protein has affinity for a particular polynucleotide sequence. Proteins which regulate DNA expression, transcription enzymes, translation enzymes are examples of such proteins. To separate such proteins from a mixture, a 3'-O-substituted polynucleotide having affinity for the protein of interest is selected.

Once a suitable solid support bound 3'-O-substituted polynucleotide is selected for the desired target biomolecule, the mixture containing the target biomolecule is contacted with the solid support bound 3'-O-substituted polynucleotide. For example, the solid support bound 3'-O-substituted polynucleotide can be added to a solution such as an aqueous solution containing the solubilized mixture. The solid support bound 3'-O-substituted polynucleotide and mixture are contacted under conditions suitable for binding between the 3'-O-substituted polynucleotide and the target biomolecule. Conditions suitable for binding will vary according to the target and can be readily determined for each target biomolecule by one of ordinary skill in the art.

Once the target biomolecule is attached to the solid support bound 3'-O-substituted polynucleotide, i.e., "captured", the solid support is separated from the mixture by any suitable means, such as filtration. When being filtered, the solid support is preferably washed with a suitable solvent to remove unbound impurities without releasing the target biomolecule. After washing, the captured target can be separated from the solid support bound 3'-O-substituted polynucleotide by any suitable means. When the captured biomolecule is a polynucleotide, the duplex can be denatured by exposing to a suitable temperature, typically about 90° C., thereby releasing the captured single stranded polynucleotide from the solid support bound 3'-O-substituted polynucleotide. The solid support can then be separated from the released target polynucleotide by, for example, filtration. When the captured biomolecule is a protein, the solid support is washed with a suitable elution solution to release the captured protein from the 3'-O-substituted polynucleotide. A suitable elution solution will depend on the protein and polynucleotide sequence.

The solid support bound 3'-O-substituted polynucleotides of the present invention can also be used to detect the presence or absence of a target biomolecule in a mixture, e.g., a mixture obtained from a tissue sample. Thus, the disclosed solid support bound 3'-O-substituted polynucleotides can be used to determine whether a particular tissue type expresses messenger RNA having a particular sequence or a particular protein known to bind with polynucleotide sequence. A 3'-O-substituted polynucleotide is selected which selectively binds to the target biomolecule of interest (e.g., protein, RNA, cDNA or single stranded DNA). Once a suitable 3'-O-substituted polynucleotide is selected for the desired target biomolecule, the mixture is contacted with the solid support having the selected 3'-O-substituted polynucleotide bound thereto under conditions suitable for binding between the 3'-O-substituted polynucleotide and the target biomolecule. The solid support bound 3'-O-substituted polynucleotide is then separated from the mixture and assessed by any suitable means to detect the presence or absence of target molecule attached to the solid support bound 3'-O-substituted polynucleotide. Alternatively, the solid support bound 3'-O-substituted polynucleotide can be subjected to conditions suitable for separating the bound target from the solid support before assessing for its presence or absence, as described above.

Alternatively, the disclosed solid support bound 3'-O-substituted polynucleotides can be used to identify new proteins which bind to a particular polynucleotide sequence. The 3'-O-substituted polynucleotide having the sequence of interest is prepared and attached to a solid support, as described above. A biological sample to be assessed is then contacted with the solid support bound 3'-O-substituted polynucleotide under conditions which are believed to be suitable for binding between the 3'-O-substituted polynucleotide and target proteins. The presence or absence of captured protein is then assessed, as described above. Any captured protein can then be isolated and characterized. It is to be understood that the precise conditions necessary to bind an unknown may not be known and that the same sample can be assessed under multiple binding conditions.

Exemplification

EXAMPLE 1

Preparation of 3'-O-Substituted Polynucleotides

Amino functionalized Primer Solid Support from Amersham Pharmacia Biotech, Inc. was derivatized with DMT-O—$CH_2CH_2SO_2CH_2CH_2$—O—CO—$CH_2CH_2$—COO-Nitrophenyl. The loading of support was about 50 µmol/g of the solid support.

The synthesis of DMT-O-hexylphosphoramidite can be carried out by procedures described in in Seela and Kaiser, *Nucleic Acids Research* 15:3113 (1987), Wilk, et al., *Nucleic Acids Res.* 18:2065 (1990) and Nelson et al., *Nucleosides Nucleotides* 16:1951 (1997).

The DMT-O-hexylphosphoramidite was coupled to the amino functionalized solid support described above using standard phosphoramidite methodology for solid phase polynucleotide synthesis. From this product, the following 3'-O-substituted polydeoxynucleotides were prepared according to standard protocols for solid phase polydeoxynucleotide synthesis using 5'-O-DMT-2'-deoxynucleoside 3'-O-(2-cyanoethyl-N,N'-diisopropyl) phosphoramidites: GGT TGG TGT GGT TGG-OPO-(O-hexyl)-phosphate (SEQ ID NO: 1) (Thrombin binding aptamer) and TM TAT GAC TCA CTA TAG GTA ACT T-OPO-(O-hexyl)-phosphate ("SP2") (SEQ ID NO: 2). The crude products were analyzed by ion exchange HPLC and MALDITOF mass spectrometer and then purified by ion exchange chromatography. The desired pooled fractions were desalted to remove excess sodium chloride and resulting products were re-analyzed by Ion Exchange HPLC and MALDITOF. The purity of these materials was found to be greater than 90% with expected molecular weight. Thrombin Binding Aptamer with linker: molecular weight was 4973 and purity by Ion-Exchange HPLC was 94.4%; and SP2 Oligonucleotide with linker: molecular weight was 7906 and purity by Ion-Exchange HPLC was 96.7%

EXAMPLE 2

Immobilization of 3'-O-Substituted Polynucleotides Onto Amino-Sepharose Resin

Amino-Sepharose resin was obtained from Amersham Pharmacia Biotech. Prior to use this support was washed with water (3× of resin), with 0.5 M sodium chloride solution (3×) and again with water (5×).

Non-Specific Binding Studies:

Approximately 3.0 ml of the washed resin was placed in plastic vial along with about 130.0 optical units (OD) of oligonucleotide D(TAA TAT GAC TCA CTA TAG GTA ACT T)-O-PO-(O-hexyl)-phosphate solution. This suspension was allowed to stand at room temperature for 20 hours with occasional mixing. In this suspension, coupling reagent EDC was not added.

The resin was transferred to sintered glass funnel; the liquid was drained and collected in a graduated tube. Subsequently the resin was washed with water, 2.0 M sodium chloride containing 10 mM sodium hydroxide solutions (3×12 ml), water (2×12 ml) and finally with the sodium chloride solution (3×11 ml).

Absorptions were measured at 260 nm using APB spectrophotometer. The following measurement were obtained:
1. Total absorption of the drained liquid and water washings was 0.022.
2. Total absorption of the NaCl/NaOH washing was 126.46.
3. Total absorption of the water washings was 1.62.
4. Total absorption of the of the NaCl and NaOH washings was 1.56.

Total absorption obtained from the washings: 129.66 OD

This result indicates that there is non-specific binding of oligonucleotide onto the amino-Sepharose which can be completely removed by washing with sodium chloride solution.

Covalent or Specific Linking of Oligonucleotides:

10 OD units of Thrombin Binding Aptamer oligonucleotide derivative (0.545 ml) was added to 220 ml of the washed, amino sepharose resin, followed by 200 ml of a 0.1 M EDC/0.1 M N-methyl-imidazole solution at pH 6. This suspension was incubated at room temperature for 3 days and then kept at 5° C. for 2 days.

A small sample of the resin was removed and washed with a 2.0 M sodium chloride in 10 mM sodium hydroxide solution until the absorption of wash solution gave 0.003 reading at 260 nm. The resin was then washed with Milli-Q water. Approximately 2.5 ml of the resin was then treated with 1.5 ml 1.0 N hydrochloric acid solution at 45 E C for 60 minutes. After cooling to room temperature and centrifugation, 500:1 of the clear solution was removed, diluted to 1.0 ml and its absorption was measured at 260 nm and found to be 0.130 OD. Hence, total OD released in the solution=0.39 OD (1.5 ml) from 2.5 ml of the resin. Loading of the resin=0.156 OD of oligonucleotide/ml of the resin. From this result, the concentration of oligonucleotide loaded onto the resin was calculated to be 1.04 µM.

About 220 ml washed resin was placed in a plastic container. 3600 OD units of Thrombin Binding Aptamer oligonucleotide GGT TGG TGT GGT TGG-OPO-O-hexylphosphate was added to this container and mixed. The coupling solution (200 ml of 0.1 M EDC/0.1 M N-methylimidazole, pH 6) was then added and solution was incubated at room temperature for 3 days. An aliquot was removed and washed with sodium chloride solution, sodium hydroxide solution, water and again with the sodium chloride and sodium hydroxide solution until no absorption at 260 nM was observed in the washings. The resin was then washed with water to remove sodium hydroxide.

500 µl of the resin was then incubated with 2.0 ml of 1.0 N HCl solution for 1.5 hours. The absorption of the resulting clear solution was measured and was found give loading 3.0 OD/ml of resin. The bulk resin was kept at 5 E C for additional 2 days and the entire resin was then washed with 2.5 L of 2.0 M sodium chloride, 10 mM sodium hydroxide, 1.0 L sodium chloride and 10 mM sodium hydroxide; absorption of the washing was found to be 0.002 OD. Finally sodium chloride and base was removed by washing with 500 ml Milli-Q water. Loading was again determined by incubating about 1.0 ml of the washed resin in 2.0 ml of 1.0 N HCl for 60 minutes at 45 EC. Absorption of the clear liquid was measured and found to give loading 4.8 OD/ml of the resin. From this result, the concentration of oligonucleotide loaded onto the resin was calculated to be 32.0 µM.

Approximately 30 ml washed amino-sepharose resin was incubated at room temperature with 25 ml solution of 0.1 M EDC/0.1 M N-methylimidazole containing 100 OD unit of SP2 oligonucleotide. After 40 hours incubation, an aliquot of the resin was taken out and washed with a solution of 2.0 M NaCl/10 mM NaOH until there was no absorption at 260 nM in the washing. Loading of this was determined as described above and was found to be 1.78 µM. The bulk material was washed following the above procedure. Again loading was determined and was found to be approximately 1.75 µM concentration.

Approximately 30 ml washed resin was incubated at room temperature with 25 ml solution of 0.1 M EDC/0.1 M N-methylimidazole containing 160 OD unit of SP2 oligonucleotide. Loading was estimated as described above after the second day (about 12 µM), fourth day (about 23 µM), fifth day (about 25 µM) and sixth day (about 26 µM M). Final loading of the bulk material before capping was found to be about 27 µM.

About 7–8 ml of Thrombin binding aptamer loaded onto resin was used for the stability experiment. The loading of this resin was about 32 µM before capping. This resin was washed with 40 ml solution of 1.0 M NaOH (10×) and water (40 ml×3). Loading of this material was determined and was found to be about 31 µM. Then the resin was washed with 40 ml solution 1.0 M NaOH (20×) followed by water (40 ml×3) and loading was determined to be about 30.8 µM. Washings with 1.0 M NaOH were repeated 20 times with 40 ml. After washing with water, loading was determined again and was found to be about 30.8 µM. These experiment indicate that there is no significant release of material by strong basic solution.

EXAMPLE 3

Capping With Buffered Acetic Acid Solution of the Free Amino Groups on the Loaded Amino Sepharose 500 ml solution of acetic acid (0.2 M) was prepared in de-ionized water and the pH of this solution was adjusted to 6.0 by adding N-methylimidazole. Approximately equal volume of this solution was added to the resin loaded with oligonucleotide. The suspension was mixed and solid EDC (coupling reagent) was added to a final concentration of 0.1 M.

After 20 hours incubation, a small sample was removed. Each sample was washed with water (20 ml×3), 1.0 M NaOH (20 ml×3), 1.0 M NaCl/10 mM NaOH (20 ml×3) and finally with water (20 ml×2). The washed sample was treated with ninhydrin solution at 50 degrees C. for 5 minutes. No free amine function was detected.

While this invention has been particularly shown and described with references to preferred embodiments thereof, it will be understood by those skilled in the art that various changes in form and details may be made therein without departing from the scope of the invention encompassed by the appended claims.

What is claimed is:

1. A solid support bound polynucleotide of the formula:

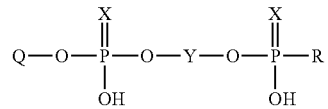

wherein:
Q is a substantially pure polynucleotide;
each X is independently O or S;
Y is an inert spacer group; and
R is a solid support;
the polynucleotide being bound to the solid support, R, via a phosphoramide linkage, or a phosphate ester linkage formed by esterifying a phosphate group with a hydroxy pendent from the solid support.

2. A solid support bound 3'-O- or 5'-O-substituted polynucleotide according to claim 1 wherein the 3'-O- or 5'-O-substituent is represented by the following structural formula:

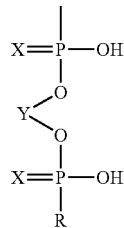

wherein:
each X is independently O or S;
Y is an inert spacer group; and
R is a solid support; and the 3'-O- and 5'-O-substituted polynucleotide are substantially pure.

3. A solid support bound polynucleotide according to claim 1 or 2, wherein Y is a straight chained hydrocarbyl group or a polyalkylene glycol group and each X is O.

4. A solid support bound polynucleotide according to claim 3, wherein Y is a C3–C10 alkylene group.

5. A solid support bound polynucleotide according to claim 1 or 2, wherein the polynucleotide is a polydeoxynucleotide.

6. A solid support bound polynucleotide according to claim 1 or 2, wherein the polynucleotide is a polyribonucleotide.

7. A solid support bound polynucleotide according to claim 1 or 2, wherein the solid support is amino sepharose, amino polystyrene, amino silica beads, silica control pore glass beads, an acrylate base amino support or a methacrylate base amino support.

8. A solid support bound polynucleotide according to claim 7, wherein the solid support is amino sepharose.

9. A solid support bound polynucleotide according to claim 1 or 2, wherein the polynucleotide selectively binds a target protein.

10. A method of preparing a solid support bound polynucleotide, said method comprising the step of esterifying or amidating the terminal phosphate of a 2'-O-, 3'-O- or 5'-O-substituted polynucleotide with an amine or hydroxyl group that is pendent from a solid support, wherein the 2'-O-, 3'-O- or the 5'-O-substituent is represented by the following structural formula:

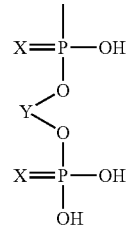

and each X is independently O or S; and Y is a straight chained hydrocarbyl group or a polyalkylene glycol group.

11. The method of claim 10 wherein the terminal phosphate is esterified or amidated in the presence of 1-(3-dimethylaminopropyl)-3-ethyl-carbodiimide.

12. The method of claim 10 or 11, wherein the solid support is, amino sepharose, amino polystyrene, amino silica beads, silica control pore glass beads, an acrylate base amino support or a methacrylate base amino support.

13. The method of claim 12, wherein the solid support is amino sepharose.

14. A method of isolating a target biomolecule from a mixture, said method comprising the steps of:
a) providing a solid support bound polynucleotide according to claim 1 or 2, wherein the polynucleotide selectively binds the target biomolecule; and
b) contacting the mixture with the solid support bound polynucleotide under conditions suitable for binding the target biomolecule to the polynucleotide.

15. The method of claim 14, wherein the target molecule is a target protein.

16. The method of claim 15, further comprising the step of separating the solid support bound polynucleotide from the mixture and eluting the target protein from the polynucleotide.

17. The method of claim 14, wherein the target molecule is a target polynucleotide which hybridizes to the solid support bound polynucleotide.

18. The method of claim 17, further comprising the steps of separating the solid support bound polynucleotide from the mixture, denaturing the target polynucleotide from the solid support bound polynucleotide and isolating the target polynucleotide.

* * * * *

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Thrombin binding aptamer

<400> SEQUENCE: 1
ggttggtgtg gttgg                                                    15

<210> SEQ ID NO 2
<211> LENGTH: 25
<212> TYPE: DNA
<213> ORGANISM: Artificial Sequence
<220> FEATURE:
<223> OTHER INFORMATION: Sequence used in non-specific binding studies

<400> SEQUENCE: 2
taatatgact cactataggt aactt                                         25

<210> SEQ ID NO 3
<211> LENGTH: 60
<212> TYPE: DNA
<213> ORGANISM: Artificial Sequence
<220> FEATURE:
<223> OTHER INFORMATION: GnRH Binding sequence

```
<400> SEQUENCE: 3
gcggcggagg gtgggctggg gctgggccgg ggggcgtgcg taagcacgta gcctcgccgc        60
```